United States Patent
Cotsarelis et al.

(10) Patent No.: US 11,033,567 B2
(45) Date of Patent: Jun. 15, 2021

(54) 5-AZA-2'-DEOXYCYTIDINE AND METHODS OF USE THEREOF FOR PROMOTING WOUND HEALING AND REGENERATION

(71) Applicant: THE TRUSTEES OF THE UNIVERSITY OF PENNSYLVANIA, Philadelphia, PA (US)

(72) Inventors: George Cotsarelis, Berwyn, PA (US); Jen-Chih Hsieh, South Setauket, NY (US); Ying Zheng, West Chester, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 301 days.

(21) Appl. No.: 15/328,057

(22) PCT Filed: Jul. 21, 2015

(86) PCT No.: PCT/US2015/041350
§ 371 (c)(1),
(2) Date: Jan. 22, 2017

(87) PCT Pub. No.: WO2016/014544
PCT Pub. Date: Jan. 28, 2016

(65) Prior Publication Data
US 2017/0209475 A1    Jul. 27, 2017

Related U.S. Application Data

(60) Provisional application No. 62/027,362, filed on Jul. 22, 2014.

(51) Int. Cl.
| | | |
|---|---|---|
| *A61K 31/706* | (2006.01) | |
| *A61K 8/60* | (2006.01) | |
| *A61Q 19/00* | (2006.01) | |
| *A61K 9/00* | (2006.01) | |

(52) U.S. Cl.
CPC .............. *A61K 31/706* (2013.01); *A61K 8/60* (2013.01); *A61K 9/0014* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,708,025 A | 1/1998 | Samid | |
| 2007/0042976 A1* | 2/2007 | Strassmann | A61K 31/53 514/43 |

OTHER PUBLICATIONS

Wang et al., Regen Med. Mar. 2010, vol. 5., No. 2, pp. 201-220. (Year: 2010).*

Wang et al. "The effects of DNA methyltransferase inhibitors and histone deacetylase inhibitors on digit regeneration in mice," Regen Med. Mar. 1, 2010, vol. 5, No. 2, pp. 201-220 (pp. 1-15 for citations). entire document.

Yang et al. "The expression of DNMT 1 in pathological scar fibroblasts and the effect of 5-aza-2-deoxyctidine on cytokines of pathologic scar fibroblasts," Wounds. May 1, 2014, vol. 26, No. 5, pp. 139-146.

Mann et al. "Regulation of myofibroblast transdifferentiation by DNA methylation and MeCPS implications for wound healing and fibrogenesis,"Cell Death and Differentiation, 2007, vol. 14, pp. 275-285.

Ateeq et al. "Pharmacological inhibition of DNA Methylation Induces Proinvasive and Prometastatic Genes in Vitro and inVivo1,"Neoplasia, Mar. 1, 2008, vol. 10 pp. 266-278.

* cited by examiner

*Primary Examiner* — Traviss C McIntosh, III
(74) *Attorney, Agent, or Firm* — Mark S. Cohen; Pearl Cohen Zedek Latzer Baratz LLP (57) ABSTRACT

This invention is directed to compositions for promoting wound healing and regeneration and methods of use thereof. In one aspect, methods for promoting wound healing in a subject are provided, the methods comprising: administering a therapeutically effective amount of a DNA methyl transferase inhibitors (DNMT) to the subject. In another aspect, methods for reducing scarring during healing of a skin wound are provided, the methods comprising: administering a therapeutically effective amount of a DNMT inhibitor.

22 Claims, 4 Drawing Sheets

5-AZA-2'-DEOXYCYTIDINE AND METHODS OF USE THEREOF FOR PROMOTING WOUND HEALING AND REGENERATION

CROSS-REFERENCE TO RELATED APPLICATIONS

This application is a National Phase Application of PCT International Application No. PCT/US15/41350, International Filing Date Jul. 21, 2015, claiming priority of United States Patent Application(s) No(s). 62/027,362, filed Jul. 22, 2014, which is/are hereby incorporated by reference.

FIELD OF INVENTION

This invention is directed to compositions for promoting wound healing and regeneration, and methods of use thereof.

BACKGROUND OF THE INVENTION

Scars from injury to the skin cause deformity, morbidity and increased health care costs. Treating complicated acute and chronic wounds represents a persistent medical challenge, and increasingly an economic one as well, in our health-care system. Wound repair involves cell proliferation, migration, and extensive remodeling of the extracellular matrix and the dermis. In adults, wound repair occurs most of the time without tissue regeneration, often resulting in scarring, accompanied by loss of function and restriction of movement. A major difference between scarred skin and normal skin is the absence of appendageal structures such as hair follicles and sweat glands. Currently, no therapy exists to regenerate normal skin that includes hair follicles and sweat glands from a wound or scar and hence, there is an existing need for such a therapy.

The present invention addresses this need by providing DNA methyl transferase (DNMT) inhibitors, e.g., 5-aza-2'-deoxycytidine or 5-azacytidine. When inhibitors of DNMT activity (i.e., blocks DNA methylation) are administered following wound closure, enhanced hair follicle regeneration occurs, suggesting that DNA methyl transferase modulates the regeneration program in a strict temporal manner. Also demonstrated is that administration of 5-aza-2'-deoxycytidine or other related DNA methyltransferase inhibitors may promote skin regeneration in healing cutaneous wounds.

SUMMARY OF THE INVENTION

In one aspect, methods for promoting wound healing in a subject are provided, the methods comprising: administering a therapeutically effective amount of a DNA methyl transferase inhibitors (DNMT) to the subject.

In another aspect, methods for reducing scarring during healing of a skin wound are provided, the methods comprising: administering a therapeutically effective amount of a DNMT inhibitor.

In an other aspect, wound healing compositions for topical application to an external wound of a mammal are provided, the compositions comprising: a DNMT inhibitor.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

In one aspect, provided herein are methods for promoting scarless wound healing of skin wound on a subject through the topical application of a drug which alters gene expression.

In one aspect, methods for promoting wound healing in a subject are provided, the methods comprising: administering a therapeutically effective amount of a DNA methyl transferase (DNMT) inhibitor to the subject.

In another aspect, methods for reducing scarring during healing of a skin wound are provided, the methods comprising: administering a therapeutically effective amount of a DNMT inhibitor.

In an other aspect, wound healing compositions for topical application to an external wound of a mammal are provided, the compositions comprising: a DNMT inhibitor.

In certain preferred embodiments, the DNA methyl transferase inhibitor is 5-aza-2'-deoxycytidine (Aza-dC). In other embodiments, the DNMT inhibitor is 5-azacytidine. Other DNMT inhibitors include, but are not limited to, MG98, S-adenosyl-homocysteine (SAH), periodate-oxidized adenosine, 3-deazadenosine, a DNA-based inhibitor such as those described in Bigey, P et al., J. Biol. Chem (1999) 274:4594-4606, or an analogue or a combination thereof.

In a related aspect, the methods and compositions provided herein promote hair follicle regeneration following wound healing in a subject. In another related aspect, use of the compositions provided herein may inhibit DNA methylation at the times when hair follicles begin to form, thereby promoting hair follicle regeneration. In some embodiments, the methods and compositions provided herein promote hair follicle formation in a subject having a hair loss disorder. In another embodiment, the methods and compositions provided herein promote sweat gland regeneration.

As used herein, the terms "SD0", "SD1", "SD2", "SD3", "SD4", etc respectively refer to the days including, and following, scab detachment, where SD0 is the day of scab detachment, SD1 is the first day after scab detachment, SD2 the second day after scab detachment, and so on. For example, a composition provided herein is administered to the subject the day after the scab has detached (SD0). The present inventors have unexpectedly shown that when the DNA methyl transferase inhibitor, 5-aza-2'-deoxycytidine (Aza-dC) was applied to the wound site immediately following scab detachment for 2 days only, Aza-dC greatly enhanced hair follicle regeneration in healed wounds (from 3 to 8 fold) in a dose-dependent manner (see Example 4 below).

Out of the four bases that make up genomic DNA cytosine is generally the base that can be methylated, and such methylation modification of DNA is generally limited to cytosine in the nucleotide sequence represented by 5'-CG-3' (C represents cytosine, and G represents guanine. Hereinafter, the nucleotide sequence is also referred to as "CpG"), and the site to be methylated in cytosine is its position 5. In DNA replication prior to cell division, only cytosine in "CpG" of a template chain is methylated prior to replication, however, cytosine in "CpG" of a newly-generated strand is immediately methylated by the action of a methyltransferase, also referred to herein as a DNA methyl transferase. Therefore, the methylation state of DNA will be passed to new two sets of DNA even after DNA replication. Hence, it is to be understood that the term "methylated DNA" can encompass DNA with such methylation modifications.

As used herein, the term "CpG pair" refers to a double-stranded oligonucleotide in which a CpG is base-paired to a complementary CpG.

As used herein, the term "objective DNA region" (hereinafter, also referred to as an "objective region") refers to a DNA region for which presence or absence of methylation of cytosine included in the region is to be examined, and has a recognition site of one or more kinds of methylation sensitive restriction enzymes. A DNA region containing at least one cytosine in the nucleotide sequence represented by CpG which is present in a nucleotide sequence of a promoter region, an untranslated region, or a translated region (coding region) of a useful protein gene can be recited.

It is to be understood recombinant DNA or recombinant protein technology may be used to arrive at any of the compositions provided herein. It is further to be understood that the term "recombinant DNA" can encompass a DNA molecule that is comprised of segments of DNA joined together by means of molecular biology techniques. Similarly, the term "recombinant protein" can encompass a protein molecule that is expressed from recombinant DNA.

Where fusion proteins are used, it is to be understood that a "fusion protein" may encompass a protein formed by expression of a hybrid gene made by combining two gene sequences. Typically this is accomplished by cloning a cDNA into an expression vector in frame with an existing gene. The fusion partner may act as a reporter (e.g., β-gal) or may provide a tool for isolation purposes (e.g., GST).

Suitable systems for production of recombinant proteins include but are not limited to prokaryotic (e.g., *Escherichia coli*), yeast (e.g., *Saccaromyces cerevisiae*), insect (e.g., baculovirus), mammalian (e.g., Chinese hamster ovary), plant (e.g., safflower), and cell-free systems (e.g., rabbit reticulocyte).

The term "coding region" refers to nucleotide sequences that encode the amino acid sequences found in the nascent polypeptide as a result of translation of an mRNA molecule. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

It will be appreciated that the term "amino acid sequence" and like terms, such as "polypeptide" or "protein," are not meant to limit the amino acid sequence to the complete, native amino acid sequence associated with the recited protein molecule. The term "wild-type" can encompass a gene or gene product that has the characteristics of that gene or gene product when isolated from a naturally occurring source. A wild-type gene is that which is most frequently observed in a population and is thus arbitrarily designated the "normal" or "wild-type" form of the gene.

In contrast, as a skilled artisan will appreciate, the terms "modified," "mutant," and "variant" can encompass a gene or gene product that displays modifications in sequence and/or functional properties (i.e., altered characteristics) when compared to the wild-type gene or gene product. It is noted that naturally occurring mutants can be isolated; these are identified by the fact that they have altered characteristics when compared to the wild-type gene or gene product.

It is to be understood that the term "conservative substitution" can encompass a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co. [1981]). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" can encompass a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.).

In some embodiments, recombinant protein techniques are used to generate the polypeptides used in the compositions and methods herein. In some embodiments, recombinant protein techniques are used for the generation of large amounts of the polypeptide of the compositions and methods herein. For example, recombinant techniques are described by Bitter et al., (1987) Methods in Enzymol. 153:516-544, Studier et al., (1990) Methods in Enzymol. 185:60-89, Brisson et al., (1984) Nature 310:511-514, Takamatsu et al., (1987) EMBO J. 6:307-311, Coruzzi et al., (1984) EMBO J. 3:1671-1680 and Brogli et al., (1984) Science 224:838-843, Gurley et al., (1986) Mol. Cell. Biol. 6:559-565 and Weissbach & Weissbach, 1988, Methods for Plant Molecular Biology, Academic Press, NY, Section VIII, pp 421-463.

Polynucleotides described herein may be prepared using PCR techniques available in the art, or any other method or procedure known to one skilled in the art. For example, the procedure involves the ligation of two different DNA sequences (See, for example, "Current Protocols in Molecular Biology", eds. Ausubel et al., John Wiley & Sons, 1992).

Plasmids may be employed for use to arrive at the compositions described herein. Plasmids are well known in the art. It will be well appreciated to the skilled artisan that the term "plasmid" may encompass a small, independently replicating, piece of DNA. Similarly, the term "naked plasmid" can encompass plasmid DNA devoid of extraneous material typically used to affect transfection. The term "naked plasmid" also encompasses a plasmid that is substantially free of calcium-phosphate, DEAE-dextran, liposomes, and/or polyamines.

In some embodiments, a variety of prokaryotic or eukaryotic cells can be used as host-expression systems to express the compositions described herein. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the coding sequence of a composition provided herein; plant cell systems infected with recombinant virus expression vectors (e.g., cauliflower mosaic virus, CaMV; tobacco mosaic virus, TMV) or transformed with recombinant plasmid expression vectors, such as Ti plasmid, containing a polypeptide coding sequence of a composition provided herein.

In some embodiments, methods of purifying a composition described herein are employed for use in the methods provided herein. It will be appreciated to the skilled artisan that the term "purified", "purifying", and grammatical equivalents thereof, can encompass molecules (polynucleotides or polypeptides) that are removed from their natural environment, isolated or separated. It will also be appreciated to the skilled artisan that the term "substantially purified" molecules can be at least 50% free, preferably at least 75% free, and more preferably at least 90% free from other components with which they are naturally associated.

In some embodiments, the DNA methylation inhibitor inhibits DNA methylation transferase (DNMT) activity and blocks DNA methylation. In some embodiments, the DNA methylation inhibitor provided herein is 5'-aza-2'-deoxycytidine (Aza-dC). In another embodiment, the DNMT includes but is not limited to DNMT1, DNMT3a or DNMT3b.

DNA methylation can be detected by methods known in the art, including, but not limited to: Methylation-Specific PCR (MSP), Whole genome bisulfite sequencing (BS-Seq), the HELP assay, ChIP-on-chip assays, Restriction landmark genomic scanning, Methylated DNA immunoprecipitation (MeDIP), analogous to chromatin immunoprecipitation used to isolate methylated DNA fragments for input into DNA detection methods such as DNA microarrays (MeDIP-chip) or DNA sequencing (MeDIP-seq), Pyrosequencing of bisulfite treated DNA, Molecular break light assay for DNA adenine methyltransferase activity, Methyl Sensitive Southern Blotting, MethylCpG Binding Proteins (MBPs) and fusion proteins containing just the Methyl Binding Domain (MBD). DNA methylation can also be detected by computational models through sophisticated algorithms and methods such as those disclosed in the following: Bhasin M, et al. (August 2005. *FEBS Lett.* 579 (20): 4302-8); Bock C, et al. (March 2006. *PLoS Genet.* 2 (3): e26); Zheng H, et al. (2011. "Enhancement on the predictive power of the prediction model for human genomic DNA methylation". *International Conference on Bioinformatics and Computational Biology (BIOCOMP'*11)); Zheng H, et al. (2013. "CpGIMethPred: computational model for predicting methylation status of CpG islands in human genome". *BMC Medical Genomics*).

In one embodiment, DNA methylation rates of a DNA region can be detected using methods known in the art and described, for example, in US Patent Application Publication No. US 2010/0009376, incorporated by reference herein in its entirety.

In one embodiment, the DNA methylation inhibitor is administered at an early stage of wound healing. It is to be understood that an "early stage" of wound healing can encompass a stage that is immediately following wound closure but prior to hair follicle regeneration.

It is to be understood that the term "wound" may encompass a disruption of the normal continuity of structures caused by a physical (e.g., mechanical) force, a biological (e.g., thermic or actinic force, or a chemical means. In particular, the term "wound" encompasses wounds of the skin. The term "wound" may also encompass lesions, contused wounds, as well as incised, stab, lacerated, open, penetrating, puncture, abrasions, grazes, burns, frostbites, corrosions, wounds caused by ripping, scratching, pressure, and biting, and other types of wounds. The term may encompasses ulcerations (i.e., ulcers), such as ulcers of the skin. The term "wound" may also encompass a healing cutaneous wound.

It is to be understood that the term "wound healing" can encompass a regenerative process with the induction of an temporal and spatial healing program comprising wound closure and the processes involved in wound closure. The term "wound healing" can also encompass the processes of granulation, neovascularization, fibroblast, endothelial and epithelial cell migration, extracellular matrix deposition, re-epithelialization, and remodeling.

It will be appreciated by a skilled artisan that the term "wound closure" can encompass healing of a wound wherein sides of the wound are rejoined to form a continuous barrier (e.g., intact skin). In another embodiment, the compositions and methods provided herein promote tissue regeneration. In another embodiment, the compositions and methods provided herein limit scarring of tissues such as glia, tendons, eye tissue, ligament or skin.

It will be appreciated by a skilled artisan that the term "granulation" can encompass the process whereby small, red, grainlike prominences form on a raw surface (that of wounds or ulcers) as healing agents.

It will be appreciated by a skilled artisan that the term "neovascularization" can encompass the new growth of blood vessels with the result that the oxygen and nutrient supply is improved. Similarly, it will be appreciated by the skilled artisan that the term "angiogenesis" may encompass the vascularization process involving the development of new capillary blood vessels. It will also be appreciated that the term "cell migration" refers to the movement of cells (e.g., fibroblast, endothelial, epithelial, etc.) to the wound site.

It is to be understood that the term "extracellular matrix deposition" can encompass the secretion by cells of fibrous elements (e.g., collagen, elastin, reticulin), link proteins (e.g., fibronectin, laminin), and space filling molecules (e.g., glycosaminoglycans). It will be appreciated by the skilled artisan that the term "type I collagen" can encompass the most abundant collagen, which forms large well-organized fibrils having high tensile strength.

It will be appreciated by a skilled artisan that the term "re-epithelialization" can encompass the reformation of epithelium over a denuded surface (e.g., wound).

It will be appreciated by a skilled artisan that the term "remodeling" can encompass the replacement of and/or devascularization of granulation tissue.

It will be appreciated by a skilled artisan that the term "impaired healing capabilities" can encompass wounds that are characterized by a disturbed wound healing process. Examples of wounds with impaired healing capabilities are wounds of diabetic patients and alcoholics, wounds which are infected by microorganisms, ischemic wounds, wounds of patients suffering from deficient blood supply or venous stasis, and ulcers. It will be appreciated by a skilled artisan that the term "chronic wound" can encompass a wound that does not fully heal even after a prolonged period of time (e.g., 2 to 3 months or longer).

In one embodiment, the compositions and methods of the present invention promote skin regeneration. In another embodiment, the compositions and methods of the present invention improve the cosmetic appearance of the wound. In another embodiment, improved cosmetic appearance comprises a closer color match with surrounding skin.

It is to be understood that the compositions of the present invention can be administered by any means available in the art, including, but not limited to parenteral (e.g. intravenous, intramuscular, intranasal), oral or topical administration.

It will be understood that the terms "administering", "administration", and like terms can encompass any method which, in sound medical or cosmetic practice, delivers a composition to a subject in such a manner as to provide a positive effect on a dermatological wound, disorder, condition, or appearance. The compositions are preferably administered such that they cover the entire area to be treated. It will be further understood that the term "Direct administration" can encompass any method which, in sound medical or cosmetic practice, delivers the composition to a subject without the use of another composition, delivery agent, or device. It will be understood that the term "Indirect administration" may encompass any method which, in sound medical or cosmetic practice, delivers the composition to a subject with the use of at least one other composition, delivery agent, or device.

It is to be understood that the terms an "effective amount" or a "therapeutically effective amount" of a composition, an active agent, an ingredient, or pharmaceutically active agent or ingredient, which are synonymous herein, can encompass an amount of the composition or pharmaceutically active agent sufficient enough to have a positive effect on the affected area. Accordingly, these amounts are sufficient to positively modify the skin wound, disorder, condition, or appearance to be treated but low enough to avoid serious side effects, within the scope of sound medical or dermatological advice. A therapeutically effective amount of the composition or pharmaceutically active agent will cause a substantial relief of symptoms when administered repeatedly over time. Effective amounts of the composition or pharmaceutically active agent can vary with the stage of wound healing. When used to treat a dermatological condition or disorder, effective amounts of the pharmaceutically active agent will vary with the particular condition or conditions being treated, the severity of the condition, the duration of the treatment, the specific components of the composition being used, and like factors. It is to be understood that the term "extended period of time" can encompass the shelf life of the compositions provided herein, including time spent on the shelf at a pharmacy as well as the entire time period after sale of the compositions during which the compositions remains effective for the indicated use. As used herein, the phrase a "label claim" refers to statements made on a label or literature accompanying a pharmaceutical product for sale. In this regard, the phrase "label claim" is intended to include indications on the label, packaging, and or literature of a pharmaceutical product of the amount(s) of any active ingredient(s) present in that product. The term "pharmaceutically acceptable salts" is to be understood as encompassing salts of the active compound(s) which possess the same pharmacological activity as the active compound (s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluoonic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylio acid, undecylenic acid, naturally and synthetically derived amino acids. Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Water or oil-soluble or dispersible products are thereby obtained.

It is to be understood that the term "sensitivity" may encompass the degree of skin irritation or skin inflammation, as exemplified by parameters in suitable assays for measuring sensitivity, inflammation, irritation, and the like. One such assay is the Jordan-King assay.

It is to be understood that the terms "storage stable" or "storage-stable", which are used interchangeably, may encompass the ability of the present compositions to have a long shelf life, including time spent on the shelf at a pharmacy as well as the entire time period after sale of the composition, during which time the composition maintains its effectiveness and pharmaceutically acceptable appearance. Accordingly, the present compositions are stable in that they exhibit a minimum amount of degradation during an extended period of storage.

It is to be understood that the term "treatment" or "treating" of a skin wound, disorder, or condition may encompass alleviation of at least one symptom thereof, a reduction in the severity thereof, or the delay, prevention, or inhibition of the progression thereof. Treatment may encompass partial or complete skin regeneration with hair follicle formation. Treatment need not mean that the wound, disease, disorder, or condition is totally cured. A useful composition herein needs only to reduce the severity of a skin wound, disease, disorder, or condition, reduce the severity of symptoms associated therewith, provide improvement to a patient's quality of life, or delay, prevent, or inhibit the onset of a skin disease, disorder, or condition.

Other terms used herein are meant to be defined by their well-known meanings in the art.

The subject matter expressed herein encompass various topical compositions for treating a skin wound, disorder, disease, or condition, and to methods for treating such skin wounds, diseases, disorders, or conditions using the same. In one embodiment, in this regard, the present subject matter relates to a topical composition for treating a skin wound, disorder or condition, which comprises a DNA methylation inhibitor. In another embodiment, the composition comprises an antibiotic. In another embodiment, the composition further comprises a pharmaceutically acceptable salt or ester thereof in solution or a pharmaceutically acceptable salt thereof in suspension. In one embodiment, the composition is formulated so that it has a final pH of about 3 to about 8. In another embodiment, the DNA methylation inhibitor containing composition is in suspension. In an alternative particularly preferred embodiment, the present compositions are formulated so that one or more of the DNA methylation inhibitor, the antibiotic or a pharmaceutically acceptable salt or ester thereof, is encapsulated or entrapped in a solid or semi-solid ingredient. In another embodiment of the present subject matter, the present compositions are formulated to minimize the amount of degradates formed of the active ingredients present. In this regard, particularly preferred compositions herein are preferably capable of effectively maintaining a concentration of each of the DNA methylation inhibitor, antibiotic or a pharmaceutically acceptable salt or ester thereof, that is at least 90% of a label claim for each of these ingredients.

In one embodiment, the compositions and methods of the present invention further make use of retinoids in wound healing. Any of a wide variety of retinoids known as useful in wound healing or treating skin diseases, disorders, or conditions is contemplated as capable of being included in the present compositions. Retinoids available for use in the present inventive subject matter include all natural and synthetic retinoids. In this regard, non-limiting examples of retinoids useful in the present compositions include tazarotene, retinoic acid, tretinoin, isotretinoin, adapalene, bexarotene, alitretinoin, vitamin A, retinol, retinal, retinyl palmitate, retinyl acetate, ethyl 5-(2-(4,4-dimethylthiochroman-6-yl)ethynyl)thiophene-2-carboxylate, 6-(2-4,4-dimethylthiochroman-6-yl)-ethynyl)-3-pyridylmethanol, 2-(2-(4,4-dimethylthiochroman-6-yl)-ethynyl)-5-pyridinecarboxaldehyde, salts thereof, derivatives thereof, and mixtures thereof. Tazarotene, retinoic acid, tretinoin, and isotretinoin, as well as salts or derivatives thereof. In another embodiment, one or more of the DNA methylation inhibitor, antibiotic or a pharmaceutically acceptable salt or ester thereof, and retinoid or a pharmaceutically acceptable salt thereof in the present compositions is encapsulated or entrapped in a solid or semi-solid ingredient for inclusion in the final compositions. This encapsulation of the active ingredient(s) can help prevent reactions between the retinoid, antibiotic, and DNA methylation inhibitor components, thus promoting the storage-stability of each of these ingredients and of the topical composition as a whole.

In another embodiment, the solid or semi-solid ingredient has a melting point at about a mammal's body temperature, such as a human's body temperature. Specific solid and semi-solid ingredients useful in this regard are well known to those of ordinary skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, http://www.accessdata.fda.gov/scripts/cder/iig/index.cfm, the contents of which are hereby incorporated by reference in their entirety.

Similarly, in one embodiment one or more of the DNA methylation inhibitor, antibiotic or a pharmaceutically acceptable salt or ester thereof, and retinoid or a pharmaceutically acceptable salt thereof can be present in the final topical composition a solution, suspension, or dispersion. Preferably, the DNA methylation inhibitor component and retinoid component are present as suspensions, while the antibiotic component is present as a solution.

In one embodiment, once all of the ingredients are combined, the final compositions herein have a final viscosity of about 20,000 to about 1,000,000 centipoises. In another embodiment, the final compositions have a final viscosity of about 40,000 to about 500,000 centipoises.

In another embodiment of the present subject matter the compositions contain each of these active ingredients at a final composition pH of about 3 to about 8 sufficient to contribute to product stability. In another embodiment, the compositions provided herein are storage stable at a temperature of about 30° C. for about 2 weeks. In another embodiment, the compositions provided herein are storage stable at a temperature of about 2-8° C., or up to 25° C. for at least 6 months, with a projected shelf life of 2 years.

In one embodiment, the final topical compositions exhibit a final pH of about 3 to about 8. In a particularly preferred embodiment, the present compositions exhibit a final pH of about 3.5 to about 5.5. In a most preferred embodiment, the present compositions exhibit a final pH of about 4 to about 5 as a target. This narrowly tailored pH is in part responsible for the advanced storage stability of the present compositions in comparison to those previously known in the art. In this regard, the present compositions can remain storage stable at a temperature of up to about 25° C. for up to about 30 days, or more. In a particularly preferred embodiment, the present compositions can remain storage stable at a temperature of up to about 30° C. for at least 14 days.

In another embodiment, the present compositions remain storage stable at a refrigerated temperature of not more than 15° C. for at least 60 days. In another embodiment, the compositions remain storage stable at a refrigerated temperature of about 2° C. to about 8° C. for at least 6 months. When the separately stored the separate compositions that make the compositions for treatment of the invention are stored at a temperature of 2-8° C., or up to 25° C., the separate compositions are stable for up to about 6 months, with a projected shelf life of about 2 years.

In another embodiment, the present compositions remain storage stable when stored separately under conditions selected from the group consisting of freezer conditions of less than about 0° C., about 2° C. to about 8° C., about 8° C. to about 15° C., about 23° C. to about 27° C., up to about 25° C., and about 15° C. to about 30° C.

Emulsions, such as oil-in-water or water-in-oil systems, as well as a base (vehicle or carrier) for the topical formulation can be selected to provide effectiveness of the active ingredients and/or avoid allergic and irritating reactions (e.g., contact dermatitis) caused by ingredients of the base or by the active ingredients.

Accordingly, the present compositions may optionally further comprise an emulsifier. Non-limiting examples of emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, tragacanth gum, poly (acrylamide-jb-acrylic acid), 10-30 alkyl acrylate crosspolymers, derivatives thereof, and mixtures thereof.

Creams useful in the present compositions may also be semisolid emulsions of oil and water and are easily applied and vanish when rubbed into the skin.

Lotions useful in the present compositions include older definitions such as suspensions of powdered material (e.g., calamine) in a water or alcohol base, as well as modern lotions (e.g., some corticosteroids) such as water-based emulsions. Convenient to apply, lotions are also cool and help to dry acute inflammatory and exudative lesions.

Ointments which are useful are oleaginous and contain little if any water, feel greasy but are generally well tolerated; best used to lubricate, especially if applied over hydrated skin; they are for lesions with thick crusts, lichenification, or heaped-up scales and may be less irritating than cream for some eroded or open lesions (e.g., stasis ulcers). Drugs in ointments are often more potent than in creams.

In one embodiment, the present compositions may take the form of a gel. In this regard, the present compositions may include a gelling agent and/or a thickener. Suitable gelling agents and/or thickeners which may be useful in the present compositions include aqueous thickening agents, such as neutral, anionic, and cationic polymers, and mixtures thereof. Exemplary polymers which may be useful in the instant compositions include carboxy vinyl polymers, such as carboxypolymethylene. A thickener may be a carbomer, for example, CARBOPOL® brand Carbopol polymer. Other exemplary polymers useful in this regard include hydrophilic/hydrophobic graft copolymers, such as polymers formed as a mixture of polystyrene/microsponge/CARBOPOL. One such polymer in this regard is a dimethylacrylamide/acrylic acid/polystyrene ethyl methacrylate copolymer, for example Pharmadur® brand copolymer.

Other, non-limiting example of suitable thickeners useful herein include cellulosic polymers, such as gum arabic, gum acacia, gum tragacanth, locust bean gum, guar gum, hydroxypropyl guar, xanthan gum, cellulose gum, sclerotium gum, carageenan gum, karaya gum, cellulose gum, rosin, methylcellulose, hydroxyethylcellulose, hydroxypropylcellulose, hydroxymethylcellulose, hydroxypropylmethylcellulose, methylhydroxyethylcellulose, cetyl hydroxyethylcellulose, carboxymethylcellulose, corn starch, hydroxypropyl starch phosphate, distarch phosphate, distarch dimethylene urea, aluminum starch octenyl succinate, maltodextrin, dextran, poly (acrylamide), PEG-150 distearate, PEG-150/decyl alcohol/SMD1 copolymer, PEG-150/stearyl alcohol/SMDI copolymer, PEG-180/Laureth-50/TMMG copolymer, Polyether 1, acrylic acid/acrylamidomethyl propane sulfonic acid copolymer, acrylate/ClO-30 alkyl acrylate crosspolymer, acrylate/beheneth-25 methacrylate copolymer, acrylate/steareth-20 methacrylate copolymer, acrylate/steareth-20 copolymer, acrylate/VA crosspolymer, acrylic acid/acrylonitrogen copolymer, ammonium acryloyldimethyltaurate/beheneth-25 methacrylate copolymer, ammonium acryloyldimethyltaurate/VP copolymer, caprylic/capric triglyceride (and) sodium acrylate copolymer, PVM/MA decadiene crosspolymer, alginic acid, propylene glycol alginate, dimethicone, silica dimethyl silylate, a dimethylacrylamide/acrylic acid/polystyrene ethyl methacrylate copolymer, derivatives thereof, and mixtures thereof. Other common thickeners and/or gelling agents, such as polyacrylic polymers, may be further useful herein. These thickeners and/or gelling agents can be present in the instant compositions regardless of what form the final composition takes.

Any other non-toxic, inert and effective carrier may be used to formulate the present compositions. Well-known carriers used to formulate other therapeutic compounds for administration to humans particularly will be useful in the compositions of the present subject matter. Pharmaceutically acceptable carriers, excipients and diluents in this regard are well known to those of skill in the art, such as those described in The Merck Index, Thirteenth Edition, Budavari et al., Eds., Merck & Co., Inc., Rahway, N.J. (2001), which is incorporated by reference herein in its entirety. Examples of such useful pharmaceutically acceptable excipients, carriers and diluents include distilled water, physiological saline, Ringer's solution, dextrose solution, Hank's solution and DMSO, which are among those preferred for use in the present subject matter. These additional components, as well as effective formulations and administration procedures are well known in the art and are described in standard textbooks, such as Goodman and Gillman's: The Pharmacological Bases of Therapeutics, 8th Ed., Gilman et al. Eds. Pergatnon Press (1990) and Remington's Pharmaceutical Sciences, 17th Ed., Mack Publishing Co., Easton, Pa. (1990), both of which are incorporated by reference herein in their entirety.

Examples of excipients that can be used according to the present invention include but are not limited to a carbomer, a polyacrylic polymer, glycerin, sodium hydroxide, sodium thiosulfate, propyl gallate, an alkyl paraben, purified water, titanium dioxide, zinc oxide, and mixtures thereof.

Other ingredients which may optionally be provided in the instant topical compositions include humectants, such as propylene glycol; solvents, such as alcohol [de minimis), sun filters, such as titanium dioxide, zinc oxide, and mixtures thereof; and anti-microbial preservatives, such as methylparaben and propylparaben. The topical compositions may also include an organic or inorganic base, such as sodium hydroxide, which is used to adjust the pH of the initial components and the final product.

In this regard, the compositions discussed herein can additionally comprise remaining amounts of one or more dermatologically acceptable excipients. Non-limiting examples of dermatologically acceptable excipients useful in these compositions are those selected from the group consisting of surfactants, preservatives, emollients, humectants, fluid alkyl alcohols, thickening agents, emulsifiers, suspending agents, pH modifiers/buffering agents, chelating agents, antioxidants, sun filters, derivatives thereof, and mixtures thereof.

Accordingly, any surfactant, preservative, emollient, humectant, fluid alkyl alcohol, thickening agent, emulsifier, suspending agent, pH modifier, chelating agent, antioxidant, sun filter, or other dermatologically acceptable excipient commonly known to those of ordinary skill in the art as useful in topical compositions is contemplated as useful in the compositions described herein. Further, any non-toxic, inert, and effective topical carrier may be used to formulate the compositions described herein. Well-known carriers used to formulate other topical therapeutic compositions for administration to humans will be useful in these compositions. Examples of these components that are well known to those of skill in the art.

In addition to the DNA methylation inhibitor, antibiotic, and retinoid, the present compositions may further contain other active ingredients readily known to those of skill in the art as useful in the topical treatment of wounds, lesions, skin disorders or conditions. Exemplary additional active ingredients include, but are not limited to, additional macrolide antibiotics, bactericidal drugs, bacteriostatic drugs, cleansing agents, absorbents, anti-infective agents, anti-inflammatory agents, astringents (drying agents that precipitate protein and shrink and contract the skin), emollients (skin softeners), moisturizers, keratolytics (agents that soften, loosen, and facilitate exfoliation of the squamous cells of the epidermis), and mixtures thereof.

Exemplary macrolide antibiotics contemplated as within the scope of the present subject matter include, but are not limited to, Azithromycin, Clarithromycin, Erythromycin, Lincomycin, and mixtures thereof. The macrolides are similar in structure and activity. All the macrolides are easily absorbed and all are primarily bacteriostatic and bind to the 50S subunit of the ribosome, thus inhibiting bacterial protein synthesis. These drugs are active against aerobic and anaerobic gram-positive cocci, with the exception of enterococci, and against gram-negative anaerobes and useful in the present compositions.

Exemplary bactericidal drugs contemplated as within the scope of the present subject matter include, but are not limited to, Penicillins, cephalosporins, vancomycin, aminoglycosides, quinolones, and polymyxins.

Exemplary bacteriostatic drugs contemplated as within the scope of the present subject matter include, but are not limited to, erythromycin, tetracyclines, chloramphenicol, lincomycin, clarithromycin, azithromycin, and sulfonamides. However, it is well know that some bactericidal drugs may be bacteriostatic against certain microorganisms and vice versa.

In another embodiment, the present compositions may be used in combination with an additional pharmaceutical dosage form to enhance their effectiveness in treating a skin disease, disorder, or condition. In this regard, the present compositions may be administered as part of a regimen additionally including any other pharmaceutical, and/or pharmaceutical dosage form known in the art as effective for the treatment of a skin disorder. Accordingly, the additional active ingredient or additional pharmaceutical dosage form can be applied to a patient either directly or indirectly, and concomitantly or sequentially, with the compositions described herein.

In one embodiment, the present composition and the additional pharmaceutical dosage form can be administered to a patient at the same time. In an alternative embodiment, one of the present compositions and the additional pharmaceutical dosage form can be administered in the morning and the other can be administered in the evening.

In another embodiment, the additional pharmaceutical dosage form can be an oral pharmaceutical dosage form. In this regard, a topical dosage form can be applied to the target area of the patient, prior to, concomitantly with, or after ingestion of the oral medication.

Furthermore, the formulation may be used with other adjunct therapies and treatments, such as pre-watching with common soaps and mild detergents. However, selection is important when treating wounds, lesions or skin disorders since antibacterial soaps and abrasive soaps may increase irritation and make it difficult to use follicular drugs. Such follicular drugs may include topical antibiotics and antiseptics, as well as intralesional corticosteroids.

The present topical compositions may be formulated for storage in a substantially non-reactive package to enhance stability of the product. The non-reactive package may contain at least two storage areas, one to store the DNA methylation inhibitor-containing composition and one to store the antibiotic/retinoid composition. Non-limiting examples of non-reactive packages in this regard include a glass package, a molded or flexible plastic package, a single-dose vial, an aluminum package, a tin package, a composition cardboard package, a laminated package, a laminated pouch, a pump, and a combination thereof. Compositions cardboard packages useful in this regard include wax coated cardboard packages.

In some embodiments, the DNA methylation inhibitor-containing composition and the antibiotic/retinoid composition can be stored in the non-reactive package under a blanket of an inert gas. Non-limiting examples of inert gases useful in this regard include nitrogen gas, argon gas, and a mixture thereof.

Additionally, the use of one of these packaging systems permits the present compositions to be stored such that both the initial DNA methylation inhibitor-containing composition and the antibiotic/retinoid composition are stable at room temperature. In another embodiment, the initial DNA methylation inhibitor and antibiotic or retinoid composition requires refrigeration, while the remaining antibiotic or retinoid composition does not.

The amount of composition per single packet may range from about 0.1 mL to about 20.0 mL, preferably between about 0.5 and about 5.0 mL, or between about 1 and about 3 mL.

In a further embodiment, the topical composition of the present subject matter is administered from a dual chambered apparatus containing separate chambers to hold the DNA methylation inhibitor-containing composition and the antibiotic/retinoid composition. In one example of such an apparatus, a dispenser is able to simultaneously dose the two compositions separately contained in the chambers by pressing a dosing head, which subsequently dispenses the two compositions in approximately equal volumes.

If desired, a dispensing unit that is able to deliver the DNA methylation inhibitor-containing composition and the antibiotic/retinoid composition in a predetermined ratio.

A further embodiment for administering the topical compositions of the present subject matter is a two-compartment tube, with the DNA methylation inhibition-containing composition in one compartment and the antibiotic/retinoid composition in the other compartment. It is contemplated that the final topical composition applied from the two-compartment tube contains a predetermined ratio (e.g., 2:1 or 1:1) of the DNA methylation inhibition-containing composition to the antibiotic/retinoid composition.

In each of the packaging embodiments, the DNA methylation inhibition-containing composition and the antibiotic/retinoid composition are mixed just prior to or during administration to form the final topical composition, as is the case with the single dose package embodiment disclosed above. For example, a user dispenses the respective compositions from the chambers of a multi-chambered apparatus into his or her palm, or into a suitable mixing container, and then mixes the DNA methylation inhibition-containing composition with the antibiotic/retinoid composition to form the final topical composition prior to applying the topical composition to the affected area. In another embodiment, the user dispenses the respective compositions from the multi-chambered apparatus directly onto the affected area of skin. The DNA methylation inhibition-containing composition and the antibiotic/retinoid composition are then mixed as the user rubs the compositions into the affected area of skin.

In another embodiment, the present compositions can be administered using one or more applicators. Non-limiting examples of useful applicators in this regard include a pledget, a swab, a pad, and combinations thereof. Additionally, the present subject matter further contemplates that any of these topical compositions are provided in a package of less than 5 g topical composition as a unit of use.

The ability to formulate compositions capable of long term storage, without pre-mixing or compounding requirements until just prior to application, are also contemplated herein. Specifically, the present compositions remain unexpectedly stable in storage for periods including between about 2 weeks and about 18 months, preferably between about 3 weeks and about 15 months, more preferably between about 30 days and about 24 months.

Once-daily disposable packaging may also improve patient compliance.

The stability and effectiveness of the topical preparations may last for at least 1 to 24 months at room temperature, or under refrigeration. This improved stability provides pharmacists and other dispensers of medication with a product which no longer requires compounding at the time of dispensing. Because compounding is no longer required, homogeneity is controlled at the point of manufacture, which improves dosing and ultimately compliance.

Advantageously, the final product requires no compounding by the pharmacist. In addition, compliance with exact amounts is possible with a lessened chance of impurities entering the product and contaminating it.

It is to be understood that the term "about" can encompass, in quantitative terms, plus or minus 5%, or in another embodiment plus or minus 10%, or in another embodiment plus or minus 15%, or in another embodiment plus or minus 20%.

In one embodiment, the compositions of the present invention are administered to an animal (e.g., mouse, rat, rabbit, hamster, guinea pig, pigs, micro-pig, chicken, camel, goat, horse, cow, sheep, dog, cat, non-human primate, and human. In one embodiment, the recited applications have uses in a wide variety of hosts. In some embodiments, such hosts include, but are not limited to, human, murine, rabbit, goat, guinea pig, camel, horse, mouse, rat, hamster, pig, micro-pig, chicken, goat, cow, sheep, dog, cat, or non-human primate.

In one embodiment, farm animals are treated by the methods of the present invention including, but not limited to, pigs, cattle, dairy cows, horses, goats, sheep, chickens, turkeys, geese, ducks and related species. In one embodiment, laboratory animals are treated by the methods of the present invention including, but not limited to, rats, mice, guinea pigs, rabbits, goats, monkeys, dogs, cats and others. In one embodiment, zoo animals are treated by the methods of the present invention including, but not limited to, all vertebrate animals kept in zoos. In one embodiment, aquatic animals are treated by the methods of the present invention including, but not limited to, fish, eels, turtles, seals, penguins, sharks, whales, and related species.

In one embodiment, domesticated animals are treated by the methods of the present invention including, but not limited to, any pet, such as cats and dogs, or animal that is kept by humans, e.g., horses, cattle, pigs, goats, rabbits, chickens, turkeys, geese, ducks and the like. As used herein, the term "pigs" includes pigs, piglets, hogs, gilts, barrows, boars and sows. As used herein, the term "cattle" refers to calves, cows, dairy cows, heifers, steers and bulls.

It will be understood that the term "subject" may encompass a mammal provided herein, including a human in need of therapy for, or susceptible to, a condition or its sequelae. The subject may include dogs, cats, pigs, cows, sheep, goats, horses, rats, mice, humans and other animals, as further provided herein. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods
Identification of DNA Methylation Pattern Changes Correlated with Skin Regeneration:

To identify such changes in the DNA methylation patterns, full-thickness skin wounds, of a size of 1.2 cm×1.2 cm, were created in C57B mice by excising all skin layers down to the muscle layer. The wounded mice were divided into two groups: in one group the wounds were left open without any dressing and treatment (Open wound group), while the wounds in the other group the wounds were covered with Tegaderm dressing for 7 days post-wounding (Occluded wound group). The Tegaderm dressing was removed from the occluded wound groups 7 days after wounding. The mice were left in the cages until wound closure and re-epithelialization.

On the day the scab detached from the healed wound (SD0), the skin tissues within the healed wounds were excised from each mouse, and the peripheral region of each healed wound tissue was trimmed away and discarded. The remaining central region of the wound tissue was treated with dispase solution at 4° C. overnight. The epidermis was separated from dermis, and the genomic DNA was extracted from both layers using Qiagen genomic DNA extraction and purification kit. Genomic DNAs were analyzed by quantitative PCR to determine the extent of DNA methylation at the promoter regions of genes of interest using SABiosciences EpiTEch Methyl qPCR Array. Two categories of genes were focused on: stem cells transcription factors and Wnt signaling pathways.

Identification of DNA Methylation Pattern Changes in Candidate Genes in the IGF, EGF, Shh Signaling Pathways and Genes Identified Previously to Change Expression Level in Regenerative Healing Compared to Non-Regenerative Healing To identify changes in the DNA methylation patterns, full-thickness skin wounds were created in the open wound and occluded wound groups, and the genomic DNA from epidermis and dermis of the healed wound tissues was extracted using Qiagen genomic DNA extraction and purification kit as described above. The genomic DNA was prepared for analysis using custom Epitech Methyl qPCR arrays containing the promoters sequences of the genes of IGF, EGF, and Shh signaling pathways and other genes identified in previous microarray analysis. The genomic DNA was analyzed by quantitative PCR to determine the extent of DNA methylation at the promoter regions of genes of interest using SABiosciences EpiTEch Methyl qPCR Array.

Determining the Effect of Systemic Aza-dC Treatment on Wound Healing and Regeneration:

To determine of global inhibition of DNA methylation on wound healing and regeneration, C57B mice carrying full-thickness skin wounds (size of the wound: 1.2×1.2 cm) were injected with Aza-dC at daily doses ranging from 10 µg to 50 µg per gram body weight, beginning on the day of scab detachment for up to 5 consecutive days. After Aza-dC treatment, the mice were left in the cages for another 3-5 weeks before the healed wound skins were harvested to assess the number of new hair follicles in the wound. The harvested skins were treated with dispase solution at 4° C. overnight, and the epidermis was peeled off. The dermis was fixed in acetone overnight. After washing 3 times in Tris.Cl buffer (pH9.5), the fixed tissue was immersed in AP buffer (Tris.HCl buffer containing 100 mM NaCl and 5 mM $Mg^{2+}$) containing alkaline phosphatase (AP) subtract (BCIP/NBT) for 30 minutes at room temperature. The AP staining was quenched by replacing the AP substrate solution with 25 mM EDTA solution. The number of dermal papilla, as revealed by the positive AP staining, in the dermis was counted under microscope.

Determining the Effect of Topical Aza-dC Treatment on Wound Healing and Regeneration:

To determine the effect of inhibiting DNA methylation locally at the wound site on regeneration, C57B mice carrying full-thickness skin wounds (size of the wound: 1.2×1.2 cm) were treated by applying 10 µL Aza-dC (in DMSO solution) to the wounds at single daily doses ranging from 1 µg to 10 µg, beginning on the day of scab detachment for up to 5 consecutive days. After Aza-dC treatment, the mice were left in the cages for another 3-5 weeks before the healed wound skins were harvested to assess the number of new hair follicles in the wound, as described above.

Results

Figure 1:
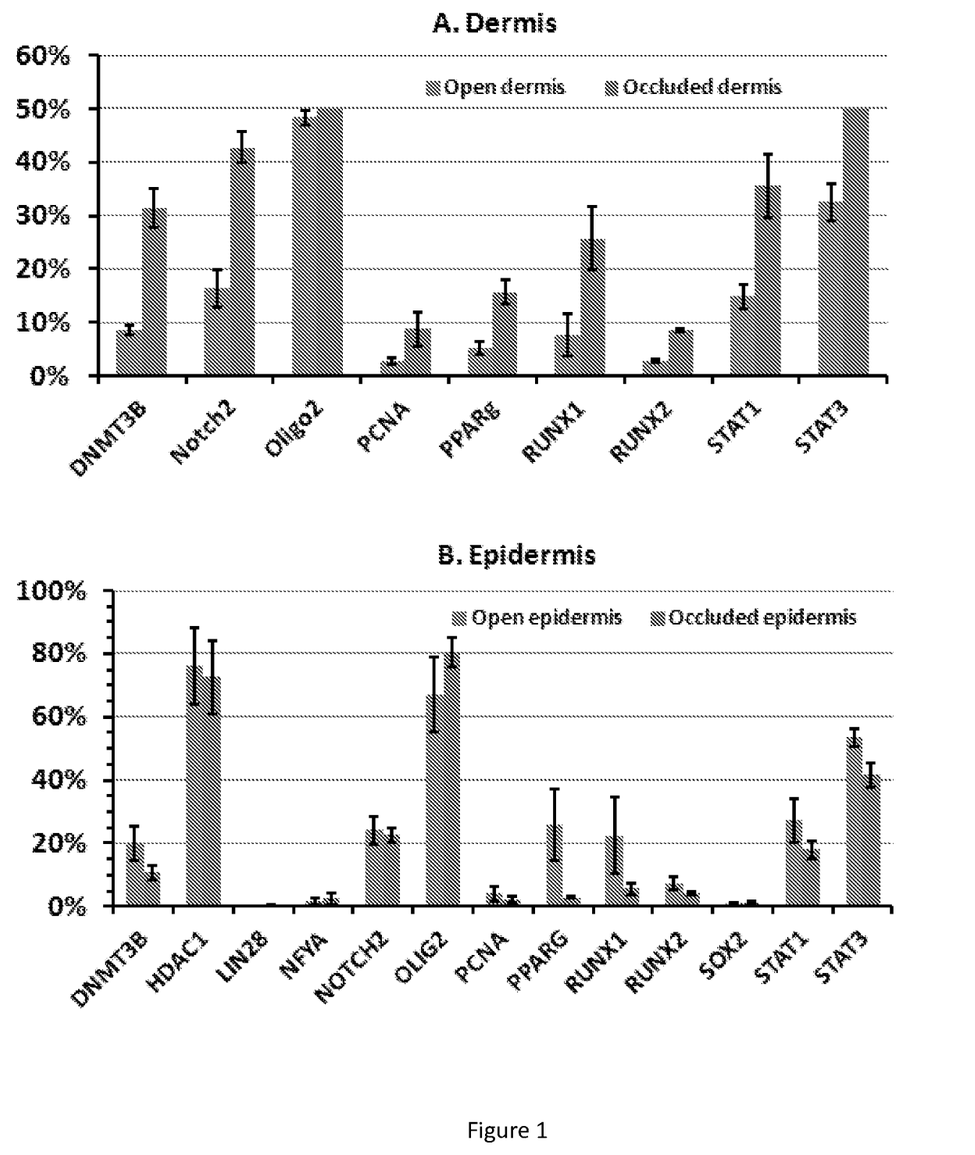
FIG. 1. Change in the DNA methylation patterns in the promoter regions of stem cell transcription factor genes in the dermis tissues (A) and the epidermis tissues (B). The Y axis shows the percentage of unmethylated DNA detected in the open wound tissues (blue bars on the left) and the occluded wound tissues (red bars on the right).

Example 1: DNA Methylation Changes in the Promoter Regions of the Stem Cell Transcription Factor Genes in Open and Occluded Wound Tissues Of the 24 stem cell transcription factor genes tested, there are several genes that showed differential methylation patterns in the regenerative (open wound) versus non-regenerative wound (occluded) healing conditions (FIG. 1). In the dermis, a significant inverse correlation between DNA methylation level and regenerative ability of the skin was observed in the promoter regions of the following genes: DNMT3B, Notch2, PCNA, PPARγ, Runx1, Runx2, Stat1 and Stat3 (FIG. 1). The reduction in the level of DNA methylation in the promoters of these genes in the non-regenerative healing suggests that up-regulation of these genes are associated with the loss of regenerative capability of the tissues. In the epidermis, a significant positive correlation between DNA methylation level and regenerative ability of the skin was observed in the promoter regions of the following genes: PPARγ, Runx1. It is interesting that the methylation patterns of these two genes showed opposite correlation with the regeneration of hair follicles in healed wound.

Figure 2:
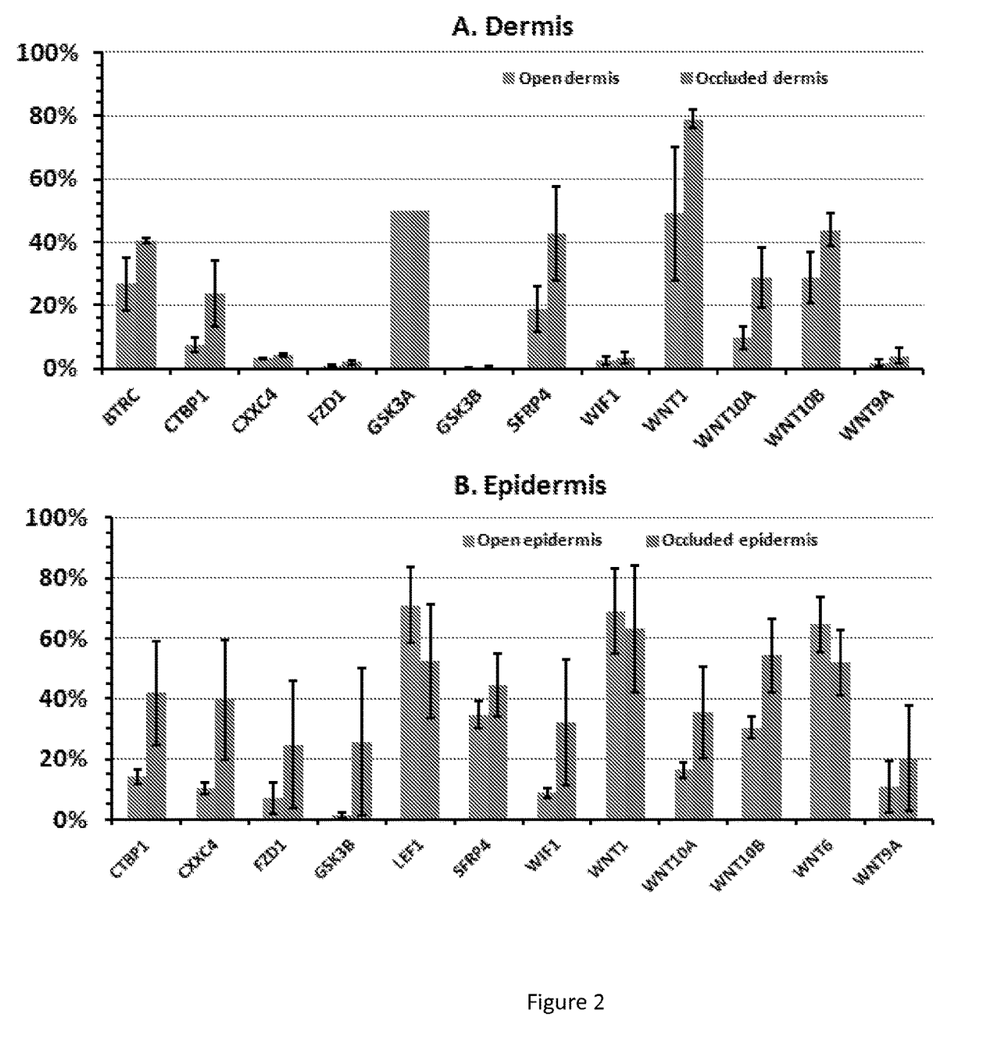
FIG. 2. Change in the DNA methylation patterns in the promoter regions of Wnt pathway genes in the dermis tissues (A) and the epidermis tissues (B). The Y axis shows the percentage of unmethylated DNA detected in the open wound tissues (blue bars on the left) and the occluded wound tissues (red bars on the right).

Example 2: DNA Methylation Changes in the Promoter Regions of the Wnt Pathways Genes in Open and Occluded Wound Tissues Of the 24 stem cell transcription factor genes tested, there are several genes that showed differential methylation patterns in the regenerative (open wound) versus non-regenerative wound (occluded) healing conditions. In the dermis, a significant inverse correlation between DNA methylation level and regenerative ability of the skin was observed in the promoter regions of the following genes: CTBP1, Wnt10a, Wnt10b, and SFRP (FIG. 2). In the epidermis, a significant inverse correlation between DNA methylation level and regenerative ability of the skin was observed in the promoter regions of the following genes: WIF1 and Wnt10a. The reduction in the level of DNA methylation in the promoters of these genes in the non-regenerative healing suggests that up-regulation of these genes are associated with the loss of regenerative capability of the tissues.

Figure 3:
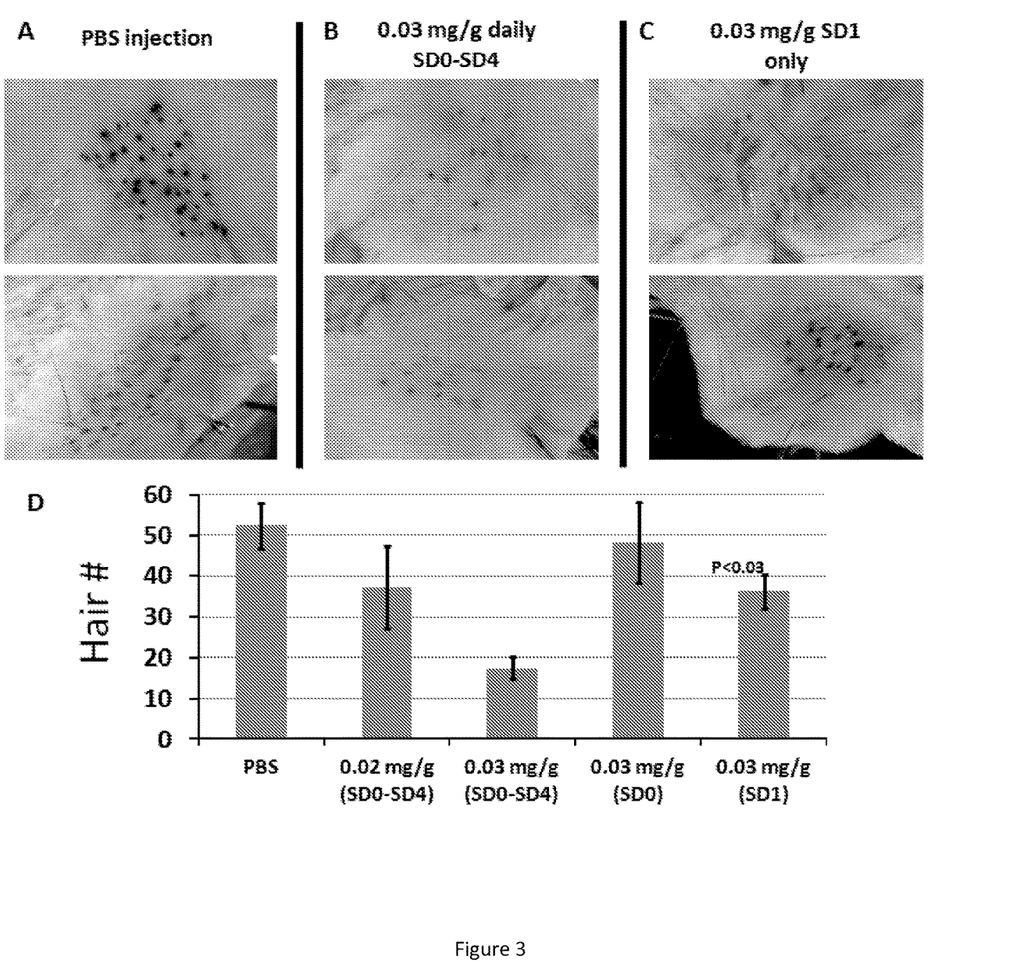
FIG. 3. Systemic 5-aza-2'-deoxycytidine (Aza-dC) treatment inhibited hair follicle regeneration in healed wounds. A-C, photos showing alkaline phosphatase staining of regenerated hair follicles in the dermis from mice injected with PBS (A), 30 µg per g body weight of Aza-dC daily from SD0 to SD4 (B), or 30 µg per g body weight of Aza-dC once on SD1 (C). (D) Systemic treatment of mice with open wound by Aza-dC consecutively for 5 days (from SD0 to SD4), or for one single day, at 30 µg per gram body weight greatly inhibited the regeneration of hair follicles.

Example 3: Systemic Treatment of DNA Methyl Transferase Inhibitor, Aza-Deoxycytidine (Aza-dC), LED to Reduced Regeneration During Wound Healing Injection of Aza-dC at 30 µg per gram body weight once a day consecutively for 5 days (from the day scab detached, SD0, to SD4) greatly inhibited the regeneration of hair follicles. The inhibitor effect on hair follicle regeneration may be due to the toxic effect of Aza-dC since the injected mice showed a reduction in their body weight compared to the PBS-injected control mice. To reduce the toxicity of Aza-dC, a single does of 30 µg (per gram body weight) of Aza-dC was injected on either SD0 or SD1. While injection on the day of scab detachment day (SD0) had no effect, a single injection on the following day (SD1) did show inhibition on hair follicle regeneration. (FIG. 3), suggesting that global inhibition of DNA methylation reduces the wound-induced regenerative capability of skin. However, it remains possible that the observed reduction in hair follicle regeneration was secondary to the toxicity exerted by Aza-dC.

Figure 4:
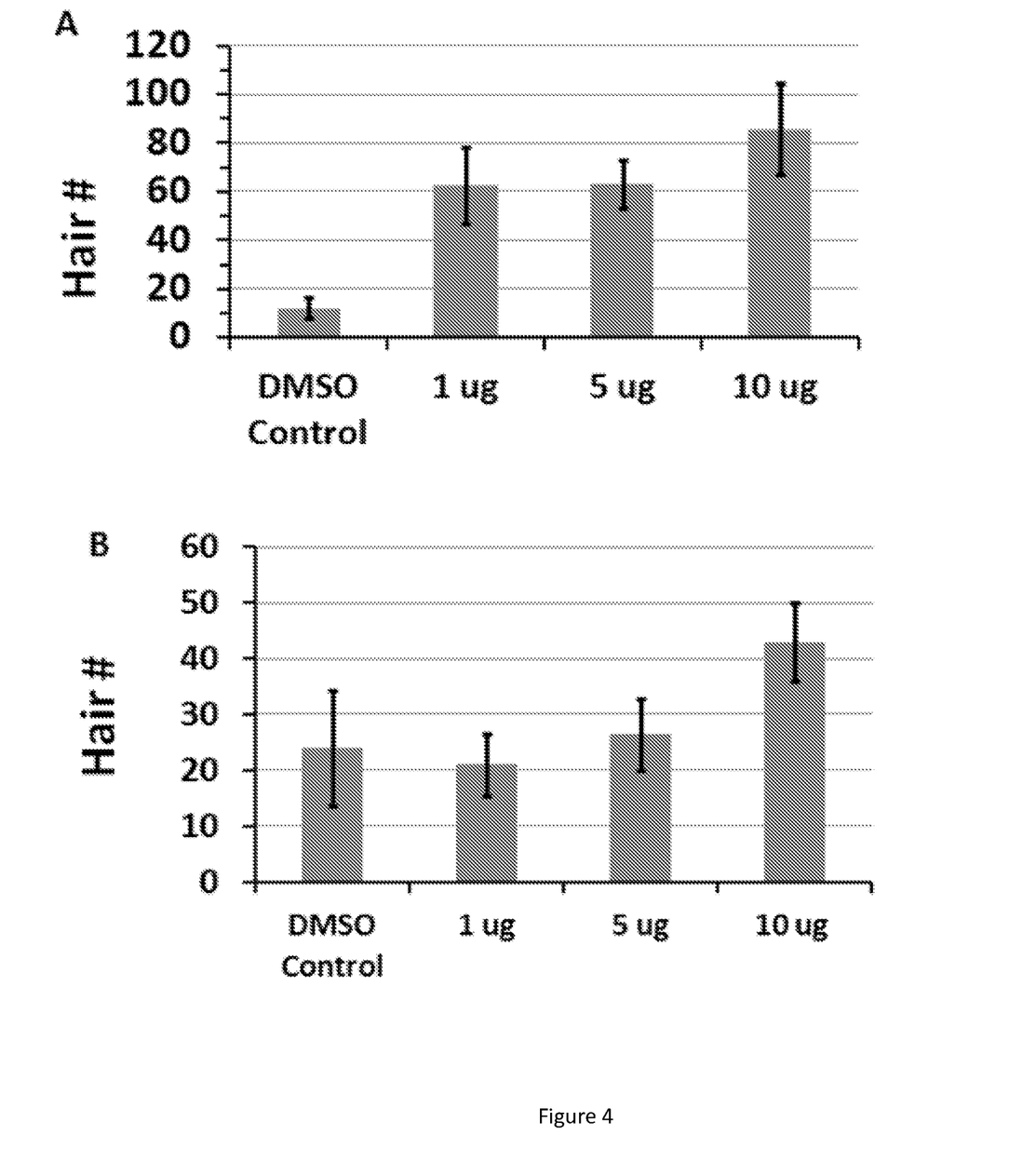
FIG. 4. Topical Aza-dC treatment enhanced hair follicle regeneration in healed wounds. (A) 10 µL of Aza-dC (dissolved in DMSO) was applied topically to the wound site, once a day, for 2 consecutive days at the time of scab detachment (SD0 & SD1). Aza-dC treatment at all doses tested greatly enhanced hair follicle (HF) neogenesis compared to the vehicle control, with the strongest enhancement seen with the highest tested dose (10 µg). (A) 10 µL of Aza-dC (dissolved in DMSO) was applied topically to the wound site, once a day, for 5 consecutive days at the time of scab detachment (SD0 to SD1). While the two lower doses (1 & 5 µg) showed little effect on the regeneration, the highest dose (10 µg) still enhanced hair follicle regeneration.

Example 4: Early Topical Treatment of DNA Methyl Transferase Inhibitor, Aza-Deoxycytidine (Aza-dC), to the Healing Wound Enhanced Regeneration After Healing To further reduce the toxicity of Aza-dC treatment, the inhibitor was applied locally to the wound sites. Unlike systemic treatment, topical application of Aza-dC exhibited little inhibitory effect on wound-induced hair follicle regeneration. When applied to the wound site immediately following scab detachment for 2 days only, Aza-dC greatly enhanced hair follicle regeneration in healed wounds (from 3 to 8 fold) in a dose-dependent manner. (FIG. 4). Therefore, up-regulation of certain genes, via inhibition of DNA methylation, at the times when hair follicles begin to form plays a critical role in the hair follicle regeneration. This stimulatory effect on regeneration was diminished when the topical treatment was extended to 5 days (from SD0 to SD4), suggesting that the expression levels of some of these genes need to be temporally controlled to support hair follicle formation.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for promoting wound healing in a subject, the method comprising topically administering to a wound in the subject a therapeutically effective amount of a DNA methylation inhibitor, wherein said DNA methylation inhibitor is administered at an early stage of wound healing, wherein the early stage of wound healing is a day of scab detachment, thereby promoting wound healing in the subject.

2. The method of claim 1, wherein said DNA methylation inhibitor is 5-aza-2' deoxycytidine (Aza-dC).

3. The method of claim 1, wherein said early stage of wound healing is immediately following wound closure but prior to hair follicle regeneration.

4. The method of claim 1, wherein said wound is a healing cutaneous wound.

5. The method of claim 1, wherein said inhibitor inhibits a DNA methyl transferase selected from DNMT1, DNMT3a or DNMT3b.

6. The method of claim 1, wherein said method promotes tissue regeneration.

7. The method of claim 6, wherein said tissue is glial tissue, eye tissue, tendon tissue, ligament tissue, or skin.

8. The method of claim 1, wherein said method promotes hair follicle regeneration.

9. The method of claim 1, wherein said method promotes sweat gland regeneration.

10. The method of claim 1, wherein said method improves the cosmetic appearance of said wound.

11. The method of claim 10, wherein improved cosmetic appearance comprises a closer color match with surrounding skin.

12. A method for reducing scarring during healing of a skin wound in a subject, comprising topically administering to the skin wound a therapeutically effective amount of a DNA methylation inhibitor, wherein said DNA methylation inhibitor is administered at an early stage of wound healing, wherein the early stage of wound healing is a day of scab detachment.

13. The method of claim 12, wherein said DNA methylation inhibitor is 5-aza-2' deoxycytidine (Aza-dC).

14. The method of claim 12, wherein said early stage of wound healing is immediately following wound closure but prior to hair follicle regeneration.

15. The method of claim 12, wherein said wound is a healing cutaneous wound.

16. The method of claim 12, wherein said inhibitor inhibits a DNA methyl transferase selected from DNMT1, DNMT3a or DNMT3b.

17. The method of claim 12, wherein said method promotes tissue regeneration.

18. The method of claim 17, wherein said tissue is glial tissue, eye tissue, tendon tissue, ligament tissue, or skin.

19. The method of claim 12, wherein said method promotes hair follicle regeneration.

20. The method of claim 12, wherein said method promotes sweat gland regeneration.

21. The method of claim 12, wherein said method improves the cos etic appearance of said wound.

22. The method of claim 21, wherein improved cosmetic appearance comprises a closer color match with surrounding tissue.

* * * * *